(12) United States Patent
Haeseler et al.

(10) Patent No.: US 7,485,669 B2
(45) Date of Patent: Feb. 3, 2009

(54) BLOCKADE OF SODIUM CHANNELS BY PHENOL DERIVATIVES

(75) Inventors: Gertrud Haeseler, Steinhude (DE); Martin Leuwer, Steinhude (DE)

(73) Assignee: B. Braun Melsungen AG (DE)

( * ) Notice: Subject to any disclaimer, the term of this patent is extended or adjusted under 35 U.S.C. 154(b) by 526 days.

(21) Appl. No.: 10/416,632

(22) PCT Filed: Nov. 13, 2001

(86) PCT No.: PCT/EP01/13081

§ 371 (c)(1),
(2), (4) Date: Sep. 8, 2003

(87) PCT Pub. No.: WO02/40005

PCT Pub. Date: May 23, 2002

(65) Prior Publication Data

US 2004/0044084 A1    Mar. 4, 2004

(30) Foreign Application Priority Data

Nov. 15, 2000  (EP) .................................. 00124870

(51) Int. Cl.
*A01N 31/00* (2006.01)
*A01M 31/08* (2006.01)
*A61K 31/045* (2006.01)
*A61K 31/05* (2006.01)

(52) U.S. Cl. ...................................... 514/730; 514/731

(58) Field of Classification Search ................. 514/730, 514/731
See application file for complete search history.

(56) References Cited

U.S. PATENT DOCUMENTS

| 1,924,169 A | 8/1933 | Stacey |
| 5,730,965 A | 3/1998 | Rapaport |
| 5,741,821 A | 4/1998 | Roufogalis et al. |
| 5,827,523 A | 10/1998 | Holland |
| 5,837,270 A | 11/1998 | Burgess |

FOREIGN PATENT DOCUMENTS

EP  0186258  7/1986

OTHER PUBLICATIONS

Haeseler, G.; Leuwer, M.; Kavan, J.; Wurz, A.; Dengler, R.; Pieperbrock, S., "Voltage-dependent block of normal and mutant muscle sodium channels by 4-Chloro-m-Cresol", 1999, British Journal of Pharmacology, 128, pp. 1259 and 1267.*
Paul, T. and Janousek, J. "New Antiarrhythmic Drugs in Pediatric Use: Propafenone", 1994, Pediatric Cardiology, vol. 15, pp. 190-197.*
Haeseler, G., et al. "Structural requirements for voltage-dependent block of muscle sodium channels by phenol derivatives", British Journal of Pharmacol.vol. 132, No. 8, 2001, pp. 1916-1924.

Haeseler, G. et al. "Phenol derivatives accelerate inactivation kinetics in one inactivation-deficient mutant human skeletal muscle Na+channel", European Journal Pharmacol, vol. 416, No. 1, 2, 2001, pp. 11-18.
Haelseler, G. et al., "Voltage-dependent block of normal and mutant muscle sodium channels by 4-Chloro-m-Cresol." British Journal of Pharmacology, vol. 128, No. 6, 1999, pp. 1259-1267.
Goodman and Gilman's, "The Pharmacological Basis of Therapeutics", Macmillan Publishing Company, New York, Chapter 41, 1985, pp. 968-970.
Trapani, G. et al., "Propofol Analogs. Synthesis, Relationships between Structure and Affinity at GABAA Receptor in Rat Brain, and Differential Electrophysiological Profile at Recombinant Human GABaA Receptors", Journal of Medicinal Chemistry, vol. 41, No. 11, pp. 1846-1854.

(Continued)

*Primary Examiner*—Sreeni Padmanabhan
*Assistant Examiner*—Kendra D Carter
(74) *Attorney, Agent, or Firm*—Connolly Bove Lodge & Hutz LLP

(57) ABSTRACT

The invention relates to a pharmaceutical composition comprising at least one phenol derivative represented by formula (I)

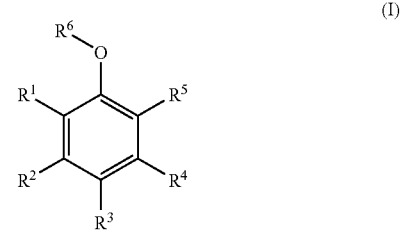

wherein
$R^1$ represents a hydrogen atom, a halogen atom or a hydrocarbon group containing up to 12 carbon atoms;
$R^2$ represents a hydrogen atom or a $C_1$-$C_7$ alkyl group; wherein
$R^1$ and $R^2$ may optionally form a carbocyclic 5- or 6-membered ring;
$R^3$ represents a hydrogen atom, a halogen atom or a $C_1$-$C_7$ alkyl group;
$R^4$ represents a hydrogen atom, a $C_1$-$C_7$ alkyl group or a halogen atom;
$R^5$ represents hydrogen atom, a halogen atom or a $C_1$-$C_7$ alkyl group; and
$R^6$ represents a hydrogen atom, a $C_1$-$C_7$ alkyl group or a $C_2$ or $C_3$ alkenyl group,
under the proviso that $R^2$ and $R^4$ can only both represent a hydrogen atom if both $R^1$ and $R^5$ represent a $C_1$-$C_7$ alkyl group and $R^3$ represents a halogen atom.

The composition is particularly useful for the blockage of sodium channels and/or influencing the kinetics of sodium channels and thus can be used as local anesthetic, antidysrhythmic, anticonvulsant/antiepilepticand spasmolytic.

5 Claims, 3 Drawing Sheets

OTHER PUBLICATIONS

Martindale The Complete Drug Reference, "Chloroxylenol", Pharmaceutical Press, Oct. 26, 2000, pp. 1111.

Ko, M-C., "Local administration of Deltasup 9-tetrahydrocannabinol attenuates capsaicin-induced thermal nociception in rhesus monkeys: aperipheral cannabinoid action", Psychopharmacology, vol. 143, No. 3, 1999, pp. 322-326.

Quan, C. et al., "Use-dependent inhibition of Na+currents by benzocain homologs", Biophysical Journal, vol. 70, No. 1, 1996, pp. 194-201.

Meerson, F.Z., et al., "Prevention of arrhythmias and cardiac fibrillation by antioxidants", Chemical Abstracts Service, Columbus, Ohio, Database accession No. 106:131070, Patologicheskaya Fiziologiya I Eksperimental'Naya Terapiya, vol. 6, 1986, pp. 3-9.

Alphin, R.S. et al., "Frequency-dependent effects of propofol on atrioventricular nodal coduction in quinea pig isolated heart; mechanisms and potential antidysrhythmic properties", Anesthesiology vol. 83, No. 2, 1995, pp. 382-394.

Maimeskulova, L. A. et al., "Antiarrhythmic effect of Rhodiola fluidum extract and P-tyrosol on experimental arrhythmia models", Chemical Abstracts Service, Columbus, Ohio, Database accession No. 129:170307, Eksperimental' Naya I klinicheskaya Farmakologiya, vol. 61, No. 2, 1998, pp. 37-40.

Elliott A.A. et al., "Voltage-dependent inhibition of RCK1 K+channels by phenol, p-cresol, and benzyl alcohol", Molecular Pharmacology, vol. 51, No. 3, 1997, pp. 475-483.

Akimoto, K., "Studies on local anesthetic effect of phenol derivatives. III Cresatin and thymol." Chemical Abstracts Service, Columbus, Ohio, Database accession No. 104:142170 HCA, Department Pharmacol., Nippon Dent. University, Tokyo, Japan, vol. 73(5), 1985, pp. 1315-1322.

* cited by examiner

FIG. 2
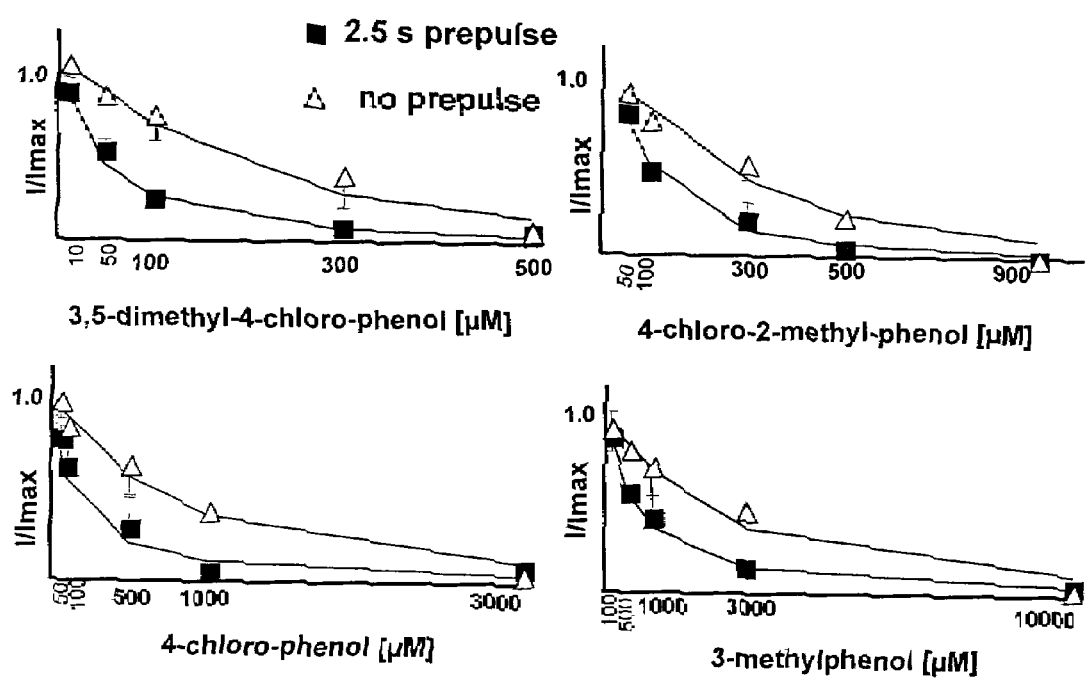
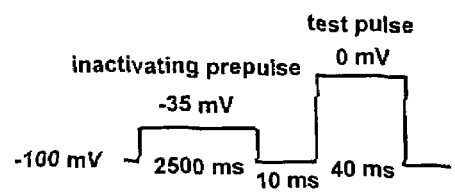

BLOCKADE OF SODIUM CHANNELS BY PHENOL DERIVATIVES

FIELD OF THE INVENTION

The invention relates to a pharmaceutical composition comprising at least one phenol derivative which is particularly useful for the blockade of sodium channels and/or influencing the kinetics of sodium channels. In the pharmaceutical field the composition can be used as local anesthetic, antidysrhythmic, anticonvulsive and spasmolytic.

BACKGROUND OF THE INVENTION

Phenol derivatives have a wide variety of clinical uses. Some are used as bacteriostatic stabilizers in parenteral drug formulations. We have recently shown that 4-chloro-3-methylphenol (4-chloro-m-cresol) and benzylalcohol both block muscle sodium channels in a voltage-dependent manner (Haeseler et al., Br. J. Pharmacol., 128 (1999) 1259-67; Haeseler et al., Br. J. Pharmacol., 130 (2000) 1321-1330). For the anesthetic propofol (2,6-di-isopropylphenol), various voltage-operated (Rehberg & Duch, Anaesthiology, 91 (1999) 512-20; Saint, Br. J. Pharmacol., 124 (1998) 655-662) and ligand-gated (Sanna et al., Br. J. Pharmacol., 126 (1999) 1444-54) channels, mainly in the central nervous system, have been identified as possible targets. Integrated into larger molecules, phenol derivatives with single substituents form the aromatic tail of most local anesthetics and class Ib antidysrhythmic drugs. The effect of the local anesthetic lidocaine (2-diethylamino-2',6'-dimethylacetanilide) on voltage-operated sodium channels in different excitable tissues has been extensively studied. Lidocaine-induced sodium channel blockade is characterized by a higher affinity of the drug for fast and slow inactivated channels compared with the resting state, and by prolonged recovery from inactivation, introducing a second, slow component representing drug dissociation from inactivated channels (Balser et al., J. Gen. Physiol., 107 (1996) 643-658; Bean et al., J. Gen. Physiol., 81 (1983) 613-642; Fan et al., J. Physiol., 81 (1996) 275-286; Scheuer, J. Gen. Physiol., 113 (1999) 3-6; Vedantham & Cannon, J. Gen. Physiol., 113 (1999) 7-16). Several studies have addressed the structural requirements for pharmacological effects (Ehring et al., J. Pharmacol. Exp. Therapeut., 244 (1988) 479-92; Sheldon et al., Mol. Pharmacol., 39 (1991) 609-614), but have not provided clues about which parts of the lidocaine molecule are responsible for its state-dependent interaction with the sodium channel. The approach of dissecting the lidocaine molecule into phenol and diethylamide (Zamponi & French, Biophys. J. 65 (1993) 2335-2347) did not take into account the fact that the aromatic group of the parent compound is a methylated phenol derivative. Although phenol block mimicked slow block of cardiac sodium channels seen with lidocaine, blocking potency was an order of magnitude lower and skeletal muscle sodium channels were only minimally affected.

SUMMARY OF THE INVENTION

It has been an object of the present invention to provide compounds having a higher potency in blocking voltage operated sodium channels such as muscle sodium channels, neuronal sodium channels and cardiac sodium channels.

It has been a further object of the present invention to provide a pharmaceutical composition, in particular a local anesthetic composition, an anticonvulsive/antiepileptic composition, an antidysrhythmic composition and a spasmolytic composition which is more effective, i.e., has an improved potency.

The above objectives were solved by a pharmaceutical or cosmetic composition comprising a phenol derivative represented by formula (I)

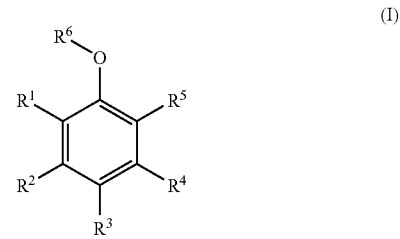

wherein
$R^1$ represents a hydrogen atom, a halogen atom or hydrocarbon group containing up to 12 carbon atoms;
$R^2$ represents a hydrogen atom or a $C_1$-$C_7$ alkyl group; wherein
$R^1$ and $R^2$ may optionally form a carbocyclic 5- or 6-membered ring;
$R^3$ represents a hydrogen atom, a halogen atom or a $C_1$-$C_7$ alkyl group;
$R^4$ represents a hydrogen atom, a $C_1$-$C_7$ alkyl group or a halogen atom;
$R^5$ represents a hydrogen atom, a halogen atom or a $C_1$-$C_7$ alkyl group; and
$R^6$ represents a hydrogen atom, a $C_1$-$C_7$ alkyl group or a $C_2$ or $C_3$ alkenyl group,
under the proviso that $R^2$ and $R^4$ can only both represent a hydrogen atom if both $R^1$ and $R^5$ represent a $C_1$-$C_7$ alkyl group and $R^3$ represents a halogen atom.

The above composition has been found to have an improved potency in blocking sodium channels and/or influencing the kinetics of sodium channels in a mammal.

Figure 1:
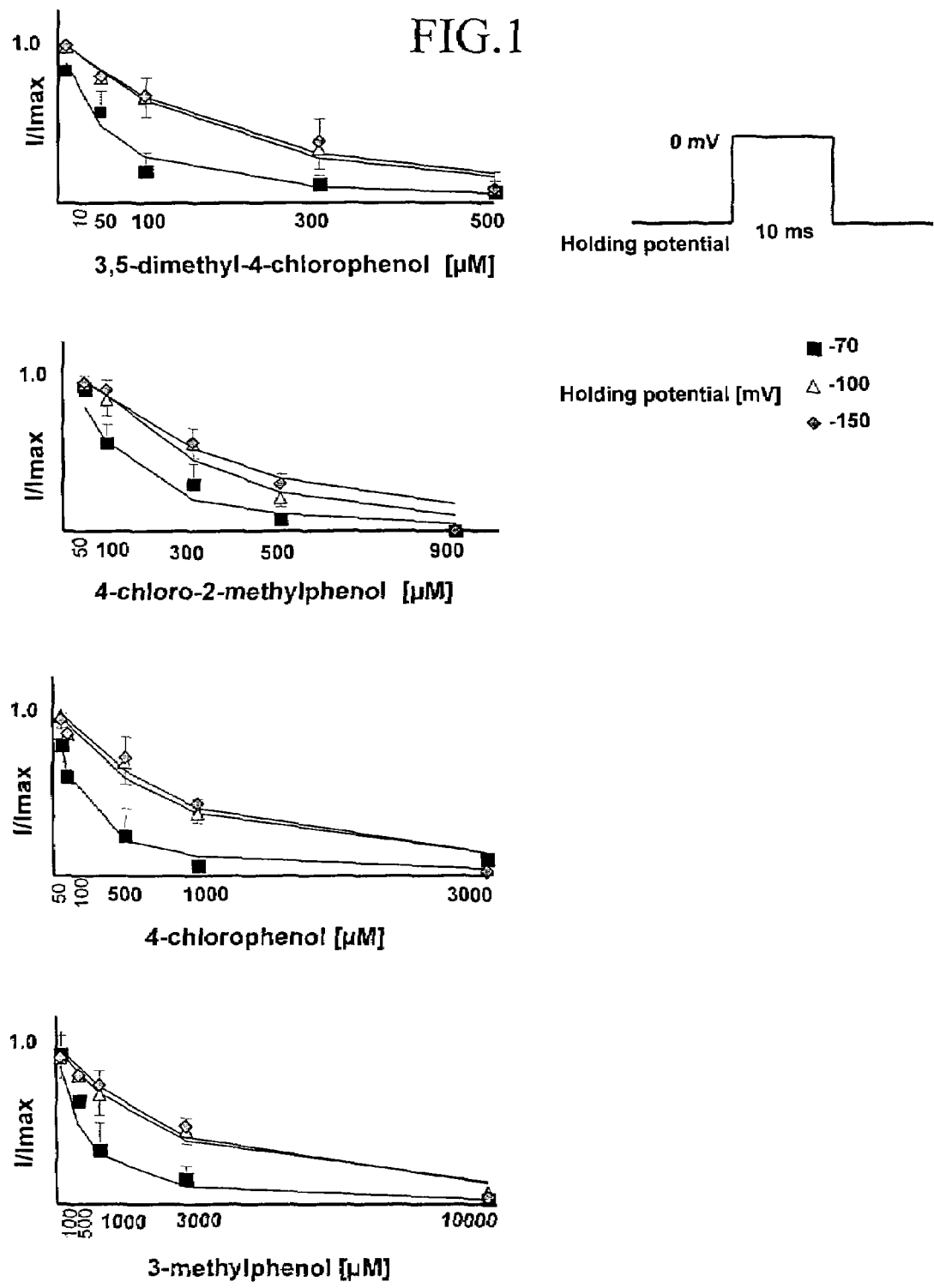
FIG. 1

Concentration-dependent reduction in test pulse current with respect to control ($I/I_{max}$, mean±SD) induced by the different compounds. The data were derived from at least four different experiments for each concentration tested. Depolarizing pulses to 0 mV (10 ms duration) were started from −150, −100, or −70 mV. Solid lines are Hill fits ($I_{Na+}$=[1+([C]/$IC_{50}$)$^{nH}$]$^{-1}$) to the data.

Concentration-response plots at −100 and −150 mV were nearly superimposable for all compounds, while the potency of the drugs was markedly increased at −70 mV.

FIG. 2

Concentration-dependent reduction in test pulse current with (filled squares) or without (empty triangles) a 2.5 s inactivating prepulse introduced before the test pulse (n>4, mean±SD). Currents were normalized to the current elicited with the same protocol in control conditions. The solid lines are Hill fits to the data. The 2.5 s prepulse uniformly enhanced sensitivity to all compounds examined.

FIG. 3

Recovery from fast inactivation assessed by a two-pulse protocol in control conditions (circles) and in the presence of 100 μM 3,5-dimethyl-4-chlorophenol (squares). The abscissa represents the recovery time interval between prepulse and test pulse (up to 100 ms), the ordinate represents the fractional current (mean±SD, n=5) after recovery from fast inactivation, induced by the prepulse in the same series. In the presence of drug, currents were normalized either to the prepulse in the presence of drug (filled symbols) or in the corresponding control conditions (empty symbols). Solid lines are exponential fits $I(t)=a_0+a_1\exp(-t/\tau_{h1})+a_2\exp(-t/\tau_{h2})$ to the fractional currents after recovery from inactivation or inactivated channel block. Without drug, the data fitted to a monoexponential. In the presence of drug, recovery was delayed and contained a second slow component of 94 ms, which made up 8% of the current amplitude.

DETAILED DESCRIPTION OF THE INVENTION

The hydrocarbon group containing up to 12 carbon atoms as defined in conjunction with substituent $R^1$ may be a straight or branched aliphatic or alicyclic group which may be substituted with at least one substituent selected from halogen, hydroxyl, and oxo groups (thus forming keto or aldehyde groups). Independently said hydrocarbon group may optionally contain at least one double-bond or said hydrocarbon group may be an aromatic group (such as a phenyl group) which may optionally be substituted with at least one straight or branched $C_1$-$C_6$ alkyl or $C_2$-$C_6$ alkenyl group. In a preferred embodiment said hydrocarbon group contains up to 7 carbon atoms, more preferably 2 to 6 carbon atoms. Preferably, said hydrocarbon group may represent a $C_1$-$C_7$ alkyl group.

Generally, in conjunction with the present invention the $C_1$-$C_7$ alkyl group as defined for substituents $R^1$ to $R^6$ denotes a branched or straight (linear) chain hydrocarbon group which may optionally be substituted with a halogen atom, a hydroxyl group or an oxo-group (=O). In another embodiment said hydrocarbon group contains 2 to 6, in a still further embodiment up to 5 carbon atoms. Preferred alkyl-groups, which may be substituted or not as mentioned above, may be selected from the group consisting of methyl, ethyl, n-propyl, iso-propyl, n-butyl, iso-butyl, sec.-butyl, tent.-butyl, and the isomers of the pentyl and hexyl-group.

It is evident that $R^1$ and $R^2$ can only form a ring if $R^1$ is neither a hydrogen nor a halogen atom. The ring which may be formed by $R^1$ and $R^2$ may further contain at least one double bond.

In a preferred embodiment the 5- or 6-membered ring formed by $R^1$ and $R^2$ is a 5- or 6-membered saturated or unsaturated carbocyclic ring, to which there can be annealed a phenyl ring, which may optionally be substituted with a $C_1$-$C_7$ alkyl group.

In terms of the present invention the halogen atoms are selected from fluorine, chlorine, bromine and iodine with chlorine and fluorine being preferred.

By a $C_2$-alkenyl group there is meant an ethenyl ($CH_2$=CH—) and by $C_3$ alkylene group there is meant a propenyl ($CH_2$=CH—$CH_2$—) group.

The substituents $R^2$ and $R^4$ can only both represent a hydrogen atom at the same time if both $R^1$ and $R^5$ represent a $C_1$-$C_7$ alkyl group and $R^3$ represents a halogen atom.

It is understood that alternative to the free phenols, i.e., if $R^6$ represents a hydrogen atom the respective alkalimetal phenolates, for instance, the sodium phenolates, may also be employed. In a preferred embodiment in the above formula (I)

$R^1$ represents a hydrogen atom, a halogen atom or a $C_1$-$C_7$ alkyl group;

$R^3$ represents a hydrogen atom, a halogen atom or a $C_1$-$C_7$ alkyl group;

$R^4$ represents a $C_1$-$C_7$ alkyl group or a halogen atom; and $R^5$ represents a hydrogen atom, a halogen atom or a $C_1$-$C_7$ alkyl group.

In an alternative embodiment in the above formula (I)

$R^1$ represents a hydrogen atom or a $C_1$-$C_7$ alkyl group;

$R^2$ represents a $C_1$-$C_7$ alkyl group; wherein $R^1$ and $R^2$ may optionally form a carbocyclic 5- or 6-membered ring;

$R^3$ represents a halogen atom or a $C_1$-$C_7$ alkyl group;

$R^4$ represents a $C_1$-$C_7$ alkyl group;

$R^5$ represents a hydrogen atom or a $C_1$-$C_7$ alkyl group; and $R^6$ represents a hydrogen atom or a $C_1$-$C_7$ alkyl group.

In a still further embodiment in the above formula (I)

$R^1$ represents a hydrogen atom;

$R^2$ represents a $C_1$-$C_7$ alkyl group;

$R^3$ represents a halogen atom;

$R^4$ represents a $C_1$-$C_7$ alkyl group;

$R^5$ represents a hydrogen atom; and $R^6$ represents a hydrogen atom.

Additionally, in the above formula (I)

$R^1$ and $R^5$ may represent a $C_1$-$C_7$ alkyl group, preferably a $C_1$-$C_5$ alkyl group, more preferably an iso-propyl-group;

$R^2$ and $R^4$ may represent a hydrogen atom;

$R^3$ may represent a halogen atom, preferably a chlorine or a bromine atom; and $R^6$ may represent a hydrogen atom or a $C_1$-$C_7$ alkyl group.

Caused by the high blocking potency in combination with interference with channel gating in voltage-gated sodium channels the compounds can be applied in low dosages as antidisrhythmic, spasmolytic, anticonvulsant/antiepileptic and local anesthetic.

The compounds according to the present invention have a higher potency in sodium channel blockade compared to conventional, state of the art compounds. For example, the $IC_{50}$ value for lidocaine block of heterologously expressed muscle sodium channels at −100 mV was 500 µM (Fan et al., J. Physiol., (1996) 275-286), compared with 150 µM for 3,5-dimethyl-4-chlorophenol, i.e., a compound according to the present invention. It has surprisingly been found that the blocking potency of phenol derivatives is increased by halogenation and by increasing the number of alkyl groups. In addition, it has been found that voltage-dependent block by all compounds retains a characteristic set of features that describes local anesthetic block.

Exemplary compounds which can be used according to the present invention are the substituted phenols (II) to (VI).

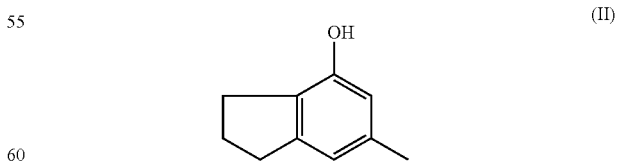

(II)

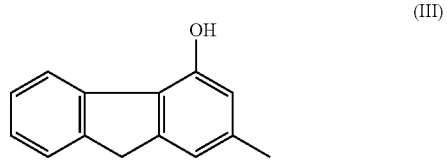

(III)

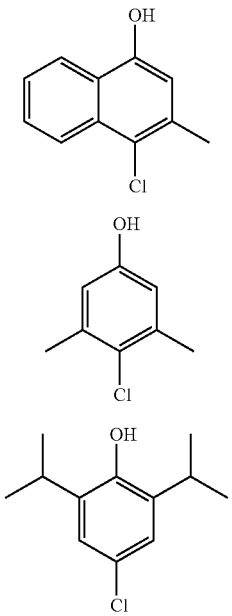

In experiments it was found that all substituted phenols blocked skeletal muscle sodium channels in a concentration-dependent manner. Compounds which are not according to the invention such as 3-methylphenol and 4-chlorophenol blocked sodium currents on depolarization from -100 mV to 0 mV with $IC_{50}$ values of 2161 µM and 666 µM, respectively. Methylation of the halogenated compound further increased potency, reducing the $IC_{50}$ to 268 µM in 4-chloro-2-methylphenol. The $IC_{50}$ was surprisingly reduced further to 150 µM in 3,5-dimethyl-4-chlorophenol, a compound falling under the scope of formula (I).

Membrane depolarization before the test depolarization significantly promoted sodium channel blockade. When depolarizations were started from −70 mV or when a 2.5 s prepulse was introduced before the test pulse inducing slow inactivation, the $IC_{50}$ was reduced more than three-fold by all compounds. The values of $K_D$ for the fast-inactivated state derived from drug-induced shifts in steady-state availability curves were 14 µM for 3,5-dimethyl-4-chlorophenol. For comparative compounds there was found 19 µM for 4-chloro-2-methylphenol, 26 µM for 4-chlorophenol and 115 µM for 3-methylphenol.

All compounds used according to the invention accelerated the current decay during depolarization and slowed recovery from fast inactivation. No relevant frequency-dependent block after depolarizing pulses applied at 10, 50, and 100 Hz was detected for any of the compounds.

All the phenol derivatives according to the present invention are effective blockers of sodium channels, such as skeletal muscle sodium channels, especially in conditions that are associated with membrane depolarization.

Typically, the pharmaceutical compositions according to the present invention can be applied in various forms such as in the form of emulsions (oil-in-water), sprays, ointments, creams, pastes and capsules. The pharmaceutical compositions thus may be in injectable form or in topically applicable form.

Injection solutions for parenteral administration comprise between about 0.1 and about 5% by weight, preferably about 0.2 to about 3% by weight and more preferably up to about 2% by weight of the phenol derivative of formula (I). For infiltrative anesthesia the solutions contain between about 0.4 and about 0.7% by weight of the active ingredient. For conduction anesthesia the solutions contain between about 1 and about 2% by weight, for epidural anesthesia between about 0.5 and about 1% by weight of the active ingredient. For local topical anesthesia the phenol derivative of formula (I) is contained in the ointment, cream or paste in an amount of about 0.5 to about 5% by weight, preferably in an amount of about 1 to about 3% by weight, typically in an amount of up to about 2% by weight.

The manufacture of parenteral solutions is conventional in the art. Due to the increased potency of the phenol derivatives the dosage is decreased significantly.

While the invention has been described in connection with a number of preferred embodiments thereof, those skilled in the art will recognize that many modifications and changes can be made therein without departing from the scope of the invention.

The present invention is further described by the experiments which follow hereinafter. The scope of the invention is not limited to these experiments.

EXPERIMENTS

The sodium channel blocking potency effects of different phenol derivatives with methyl and halogen substituents have been studied on heterologously expressed human skeletal muscle sodium channels. The phenol derivatives encompassed by formula (I) are either commercially available or can be synthesized by conventional standard laboratory methods.

Molecular Biology

Wild type α-subunits of human muscle sodium channels were heterologously expressed in human embryonic kidney (HEK 293) cells, a stable cell line since 1962 (American Tissue Culture Collection CRL 1573). Transfection was performed using calcium phosphate precipitation (Graham & Van der Eb, Virology, 52 (1973) 456-467). Permanent expression was achieved by selection for resistance to the aminoglycoside antibiotic geneticin G418 (Life Technology, Eggenstein, Germany) (Mitotic et al., J. Physiol., 478 (1994) 395-402). Successful channel expression was verified electrophysiologically. The clone has been used in several investigations (Haeseler et al.,Br. J. Pharmacol., 128 (1999) 1259-67; Haeseler et al., Br. J. Pharmacol. 130 (2000) 1321-1330; Mitrovic et al., ibid.).

Solutions 3,5-dimethyl-4-chlorophenol (according to the invention) and 3-methylphenol (not according to the invention) were purchased from Sigma Chemicals, Deisenhofen, Germany; 4-chloro-2-methylphenol (not according to the invention) and 4-chlorophenol (not according to the invention) were from FLUKA, Deisenhofen, Germany. 3,5-Dimethyl-4-chlorophenol was prepared as a 1 M stock solution in methanol; 4-chloro-2-methylphenol, 4-chlorophenol, and 3-methylphenol were dissolved directly in the bath solution immediately before the experiments. Concentrations were calculated from the amount injected into the glass vials. Drug-containing solutions were protected from light and were vigorously vortexed for 60 min. The solution was applied via a glass polytetrafluoroethylene perfusion system and a stainless steel superfusion pipette. The bath solution contained (mM) NaCl 140, $MgCl_2$ 1.0, KCl 4.0, $CaCl_2$ 2.0, Hepes 5.0, dextrose 5.0. Patch electrodes contained (mM) $CsCl_2$ 130, $MgCl_2$ 2.0, EGTA 5.0, Hepes 10. All solutions were adjusted to 290 mosm/l by the addition of mannitol and to pH 7.4 by the addition of CsOH.

Experimental Set-Up

Standard whole-cell voltage-clamp experiments (Hamill et al., Pfuegers Arch., 391 (1981) 85-100) were performed at 20° C. Each experiment consisted of test recordings with the drug present at only one concentration, and of drug-free control recordings before and after the test. Each whole-cell patch was exposed to one test concentration only. At least four experiments were performed at each concentration. The amount of the diluent methanol corresponding to the test concentration of 3,5-dimethyl-4-chlorophenol was added to the control solution. Patched cells were lifted into the visible stream of either bath solution or test solution, applied via a two-channel superfusion pipette close to the cell. To ensure adequate adjustment of the application device, one test experiment in distilled water reducing inward sodium current to zero was performed every 6-10 experiments.

Current Recordings and Analysis

For data acquisition and further analysis we used the EPC9 digitally-controlled amplifier in combination with Pulse and Pulse Fit software (HEKA Electronics, Lambrecht, Germany). The EPC9 provides automatic subtraction of capacitive and leakage currents by means of a prepulse protocol. The data were filtered at 10 kHz and digitized at 20 µs per point. Input resistance of the patch pipettes was at 1.8-2.5 MΩ. Only small cells with capacitances of 9-15 pF were used; residual series resistance (after 50% compensation) was 1.2-2.5 MΩ; experiments with a rise in series resistance were rejected. The time constant of the voltage settling within the membrane (residual series resistance×cell capacitance) was less than 35 µs. To minimize a possible contribution of endogenous $Na^+$ channels in HEK cells that conduct with amplitudes ranging from 50 to 350 pA (Mitrovic et al., 1994, ibid.), but also to avoid large series resistance errors, only currents ranging between 1 and 6 nA were analysed. To minimize time-dependent shifts in the voltage-dependence of steady-state inactivation (Wang et al., 1996), all test experiments were performed within 5 min of patch rupture. Under these experimental conditions, time-dependent hyperpolarizing shifts in control conditions were less than −2 mV (Haeseler et al., Anesthiology, 92 (2000) 1385-92). Voltage-activated currents were studied by applying different voltage-clamp protocols. Either exponential functions [$I(t)=a_0+a_1 \exp(-t/\tau_{h1})+a_2 \exp(-t/\tau_{h2})$] or Boltzmann functions [$I/I_{max}=(1+\exp(-zF(V_{test}-V_{0.5})/RT))^{-1}$] were fitted to the data, using a non-linear least-squares Marquardt-Levenberg algorithm, yielding the time constant τ of inactivation and recovery from inactivation, the membrane potential at half-maximum channel availability ($V_{0.5}$), and the slope factor z of the steady-state availability curve. F is Faraday's constant ($9.6487 \times 10^4$ C $mol^{-1}$), R is the gas constant (8.315 J $K^{-1}$ $mol^{-1}$), and T is the temperature in degrees Kelvin. Drug effects on the peak current amplitude were assessed at different holding potentials (−70, −100 and −150 mV), or when a 2.5 s prepulse to −35 mV was introduced before the test pulse in order to induce slow inactivation. All data are presented as mean ±SD. The residual sodium current ($I_{Na+}$) in the presence of drug (with respect to the current amplitude in control solution) was plotted against the applied concentration of each drug [C]. Fits of the Hill equation [$I_{Na+}=(1+([C]/IC_{50})^{nH})^{-1}$] to the data yielded the concentration for half-maximum channel blockade ($IC_{50}$) and the Hill coefficient $n_H$.

Results

Successful $Na^+$ channel expression was verified electrophysiogically in almost all of the established whole-cell patches. In all 83 cells were included in the study. Average currents in the control experiments after depolarization from −100 mV to 0 mV were 4.9±2.1 nA.

Suppression of Peak Sodium Currents-Differences in Potency Related to Methylation and/or Halogenation of the Phenol Ring Maximum inward currents elicited by 10 ms pulses going from either −150 mV, −100 mV, or −70 mV to 0 mV were reversibly suppressed by all substances in a concentration-dependent manner. Suppression occurred within 60 s after the start of perfusion with the drug-containing solution. The currents in the presence of drug were normalized to the respective current elicited in control conditions. Normalized currents derived from at least four different experiments for each drug concentration were averaged to establish concentration-response plots (see FIG. 1).

The degree of suppression at all holding potentials increased with halogenation and with the number of methyl groups at the phenol ring. The phenol derivative 3-methylphenol, containing only one methyl group in the meta position with respect to the hydroxyl group, blocked inward sodium current at a holding potential of −150 mV, with an $IC_{50}$ value of 2395 µM.

The halogenated compound 4-chlorophenol was more potent than the methylated compound, and reduced the $IC_{50}$ to 751 µM. Methylation in addition to halogenation further increased potency, reducing the $IC_{50}$ about two-fold for each methyl group inserted into the halogenated compound (316 µM for 4-chloro-2-methylphenol and 162 µM for 3,5-dimethyl-4-chlorophenol).

Acceleration of the $Na^+$ Current Decay Phase by Phenol Derivatives

To examine the time course of $Na^+$ channel inactivation during a depolarization, 40 ms voltage steps from a holding potential of −100 mV to 0 mV were performed. The time constant of channel inactivation $\tau_h$ was obtained by fitting a single exponential to the decay of current during depolarizations: $I(t)=a_0+a_1 \exp(-t/\tau_h)$. In control conditions, $\tau_h$ was 0.43±0.08 ms (n=72). All phenol derivatives accelerated the decay of whole-cell currents. For all compounds, however, this effect was apparent only at concentrations that exceeded the $IC_{50}$ values at a holding potential of −70 mV. Values obtained for $\tau_h$ in the presence of drug were: 0.27±0.02 ms in 50 µM 3,5-dimethyl-4-chlorophenol, 0.27±0.05 ms in 100 µM 4-chloro-2-methylphenol, 0.23±0.03 ms in 500 µM 4-chlorophenol, and 0.30±0.08 ms in 1000 µM 3-methylphenol.

Effects of Phenol Derivatives on Recovery from Fast Inactivation

Figure 3:
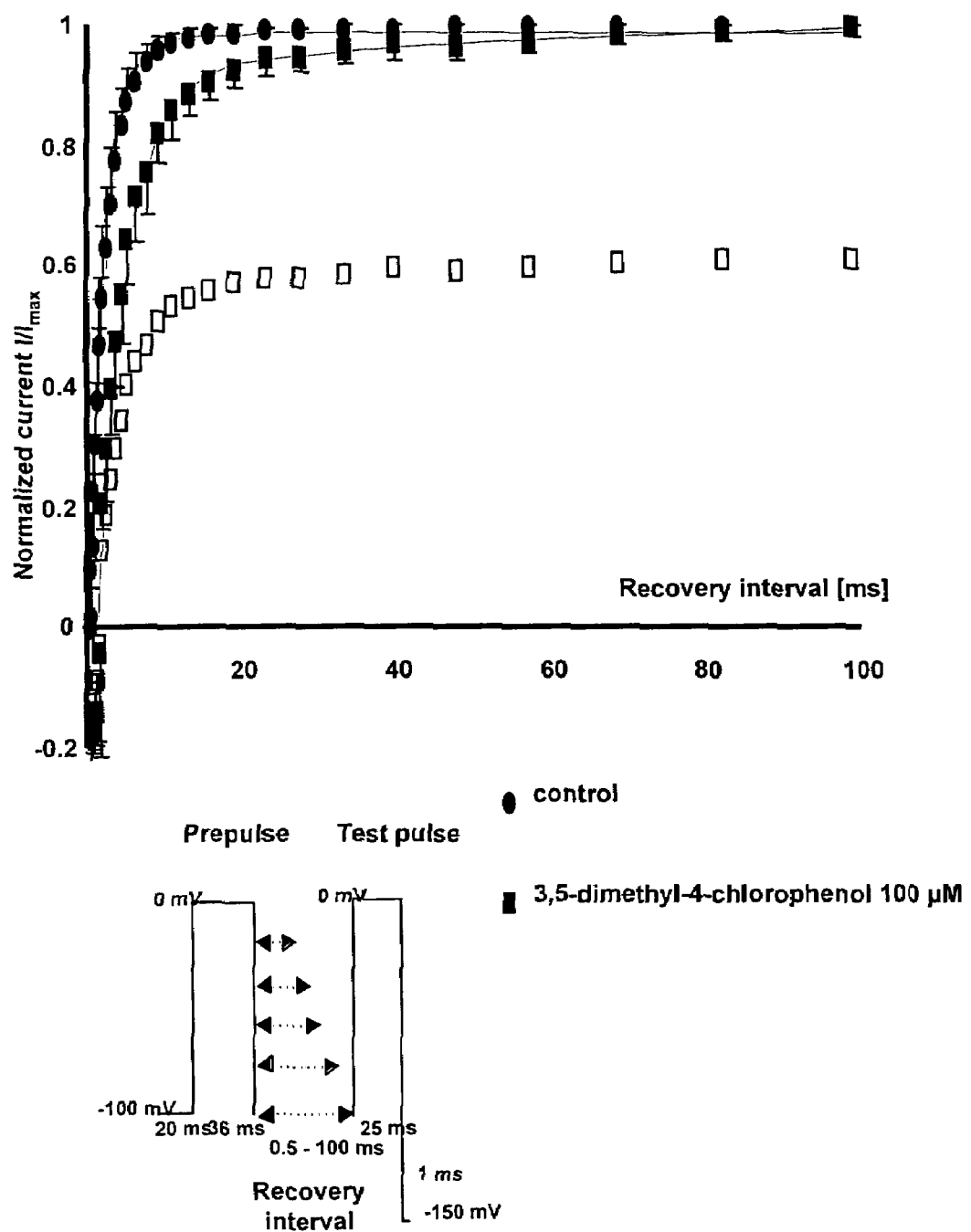

After inactivation, channel re-openings are impossible until the channels recover from inactivation, a process that requires several ms after membrane repolarization. Further information about drug effects on the stability of the fast-inactivated state or the kinetics of drug dissociation from the fast-inactivated state can be derived from the rate at which the channels recover from inactivation in the presence of the drug. The time of membrane repolarization required to remove fast inactivation was assessed at −100 mV by a two-pulse protocol with varying time intervals (up to 100 ms) between the inactivating prepulse and the test pulse (see FIG. 3). The time constants of recovery, $\tau_{rec}$, were derived from monoexponential or biexponential fits to the fractional current after recovery from inactivation, plotted against the time interval between the inactivating prepulse and the test pulse: $I(t)=a_0+a_1 \exp(-t/\tau_{rec1})+a_2 \exp(-t/\tau_{rec2})$ Without drug, the data fitted well to a monoexponential, yielding a time constant, $\tau_{rec1}$, of 2.3±0.7 ms (n=34). In the presence of drug, the fit contained a second, slow component of recovery, $\tau_{rec2}$ of 94±8 ms (3,5-dimethyl-4-chlorophenol), 36±5 ms (4-chloro-2-methylphenol), and 30±0.1 ms 4-chlorophenol and 3-methylphenol). For all drugs, however, the slow component made up less than 10% of the current amplitude at concentrations close to the $IC_{50}$ for rest block. The fast component, $\tau_{rec1}$, was prolonged to 3.8±0.8 ms in 100 μM 3,5-dimethyl-4-chlorophenol, to 4.3±1.6 ms in 300 μM 4-chloro-2-methylphenol, to 3.0±0.7 ms in 500 μM 4-chlorophenol, and to 2.8±0.6 ms in 1000 μM 3-methylphenol. FIG. 3 shows the time-course of recovery from fast inactivation with and without 100 μM 3,5-dimethyl-4-chlorophenol.

Frequency-Dependent Block

The accumulation of block during trains of depolarizing pulses indicates that the interval between pulses is too short to allow recovery of $Na^+$ channel availability. To derive an estimate of the kinetics of drug binding and unbinding during the interpulse interval, we applied series of 1-10 ms depolarizing pulses from −100 mV to 0 mV at high frequencies (10, 50, and 100 Hz).

Frequency-dependent block was defined as the additional reduction in $I_{Na+}$ for the last pulse relative to the first pulse in a test train in the presence of drug.

In control conditions, the amplitude of the last pulse relative to the first pulse in a test train was 99±1% at 10 Hz and 96±3% at 50 and 100 Hz. Neither compound induced frequency-dependent block over 10% at 10 Hz. At 50 and 100 Hz, only concentrations exceeding the $IC_{50}$ for rest block produced a small amount of frequency-dependent block. During a 100 Hz train, the additional fall relative to the first pulse was 17±5% in 300 μM 3,5-dimethyl-4-chlorophenol, 16±5% in 500 μM 4-chloro-2-methylphenol, 13±2% in 1000 μM 4-chlorophenol, and 8±2% in 3000 μM 3-methylphenol.

The invention claimed is:

1. The method for treatment of a human or animal body which comprises administering an effective amount of a phenol derivative represented by formula (VI) for the blockade of sodium channels and/or for influencing the kinetics of sodium channels:

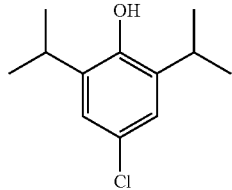

(VI)

2. The method for treatment of a human or animal body which comprises administering an effective amount of a phenol derivative represented by formula (I) for the blockade of sodium channels and/or for influencing the kinetics of sodium channels:

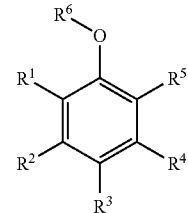

(I)

Wherein, $R^1$ and $R^5$ each represents a $C_2$-$C_6$ alkyl group;

$R^2$, $R^4$, and $R^6$ each represents a hydrogen atom, and $R^3$ represents a halogen atom.

3. The method of claim 2 wherein $R^3$ is an iodine atom.

4. The method of claim 2 wherein $R^3$ is a chlorine or bromine atom.

5. The method of claim 2 wherein an effective amount of a phenol derivative of formula (I) is administered for the treatment of dysrhyhthmia.

* * * * *